United States Patent [19]
Wood

[11] 4,306,100
[45] Dec. 15, 1981

[54] PROCESS FOR PRODUCTION OF ALKENEDIOLS

[75] Inventor: George R. Wood, Wheaton, Ill.

[73] Assignee: Standard Oil Company (Indiana), Chicago, Ill.

[21] Appl. No.: 160,082

[22] Filed: Jun. 16, 1980

[51] Int. Cl.$^3$ .............................. C07C 31/20
[52] U.S. Cl. ........................ 568/857; 570/235; 570/261
[58] Field of Search ............... 568/857, 859; 570/235, 570/261

[56] References Cited

U.S. PATENT DOCUMENTS

| | | | |
|---|---|---|---|
| 1,402,317 | 1/1922 | Rodebush | 568/859 |
| 2,299,477 | 10/1942 | Hearne et al. | |
| 2,698,347 | 12/1954 | Giraitis | 570/261 |
| 2,861,084 | 11/1958 | Starcher et al. | |
| 3,194,847 | 7/1965 | Capp et al. | 570/235 |
| 3,342,882 | 9/1967 | Costain et al. | |
| 3,641,159 | 2/1972 | Schmerling | 570/261 |
| 3,843,733 | 10/1974 | Kisaki et al. | 568/857 |
| 3,911,032 | 10/1975 | Sakomura et al. | 568/857 |
| 4,160,115 | 7/1979 | Vasey et al. | 568/857 |
| 4,164,616 | 8/1979 | Childs | 568/857 |

FOREIGN PATENT DOCUMENTS

| | | | |
|---|---|---|---|
| 451379 | 9/1948 | Canada | 570/251 |
| 2129674 | 12/1971 | Fed. Rep. of Germany | 570/261 |

OTHER PUBLICATIONS

Arganbright et al., "J. Org. Chem.", vol. 57, No. 4 (Apr. 1962), p. 1205–1208.

Primary Examiner—Joseph E. Evans
Attorney, Agent, or Firm—Stephen L. Hensley; William T. McClain; William H. Magidson

[57] ABSTRACT

Alkenediols are produced by hydrolysis of a dibromoalkenes in the presence of alkali metal formate. In a preferred embodiment, alkenediols, and particularly 2-butene-1,4-diol, are produced in a series of steps comprising bromination of conjugated diene with cupric bromide, hydrolysis of the resulting dibromobutenes to alkenediols in the presence of alkali metal formate, and regeneration of cupric bromide and alkali metal formate such that only conjugated diene, oxygen and water are consumed.

21 Claims, 1 Drawing Figure

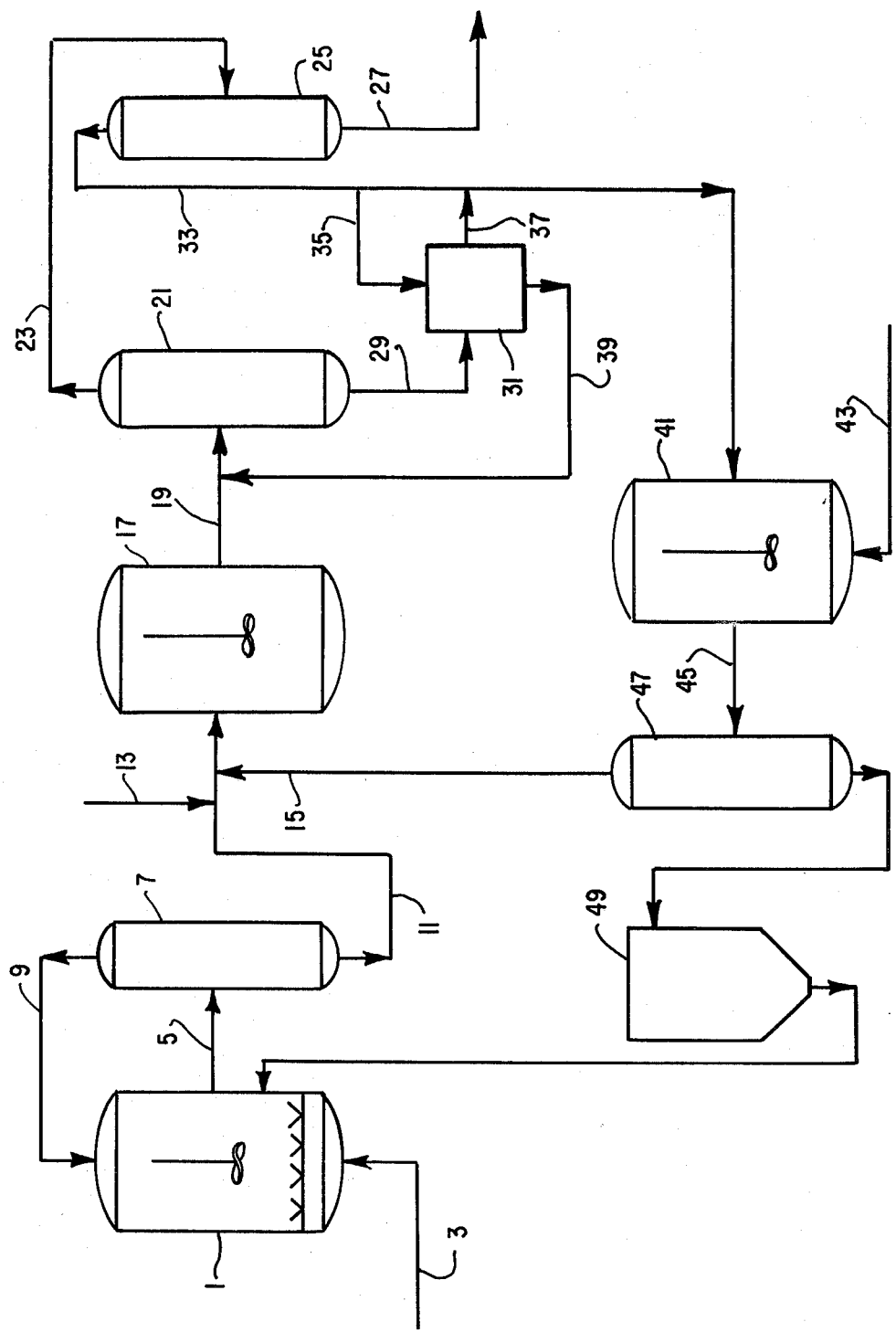

PROCESS FOR PRODUCTION OF ALKENEDIOLS

BACKGROUND OF THE INVENTION

This invention relates to the production of alkenediols. In a specific aspect, the invention relates to the production of alkenediols, and particularly 2-butene-1,4-diol, according to a series of reactions in which only conjugated diene, water and oxygen are consumed.

2-butene-1,4-diol is well known as a solvent in various chemical processes and as a starting material for the production of 2,5-dihydrofuran, another useful solvent. Further, 2-butene-1,4-diol can be hydrogenated to 1,4-butanediol which is used in the production of tetrahydrofuran, certain polyesters and polyurethanes.

In the past, a number of methods have been proposed for the production of 2-butene-1,4-diol and other alkenediols. One such method, disclosed in Sakomura et al., U.S. Pat. No. 3,911,032 (Oct. 7, 1975), involves hydrolysis of 1,4-dichloro-2-butene in an aqueous solution of alkali metal formate. According to this proposal, conversion of 1,4-dichloro-2-butene to 2-butene-1,4-diol is substantially complete. Further, substantially complete conversion of mixed dichlorobutene isomers to 2-butene-1,4-diol can be accomplished by conducting the hydrolysis reaction in the presence of elemental copper, iron, or zinc or a halide, formate, oxide, carbonyl or hydroxide thereof.

Vasey et al., U.S. Pat. No. 4,160,115 (July 3, 1979) discloses preparation of 2-butene-1,4-diol by reaction of butadiene with water and oxygen in the presence of copper, nickel, cobalt, chromium, manganese, molybdenum or a halide or organic acid salt thereof. The reaction is conducted at 50° to about 150° C., preferably in a water-miscible solvent.

Childs, U.S. Pat. No. 4,164,616 (Aug. 14, 1979) discloses preparation of alkanediols and alkenediols by a series of reactions involving halogenation of conjugated diene with molecular chlorine, bromine or iodine; acetolysis of the result in the presence of a salt of an alkali metal or alkaline earth metal, dissolved or dispersed in an organic acid solvent, to form diacetoxyalkene; hydrogenation of diacetoxyalkene to the corresponding diacetoxyalkane; hydrolysis of diacetoxyalkane to 1,4-alkanediol, preferably under basic conditions using an alkali or alkaline earth hydroxide; and regeneration of starting materials by passing an electric current through an aqueous solution of by-product metal halide from the acetolysis step to regenerate halogen for use in the halogenation step, hydrogen for use in the hydrogenation step and metal hydroxide for use in the hydrolysis step. The sequence of the hydrogenation and hydrolysis steps may be reversed according to the patentee.

Although alkenediols can be obtained according to the above-described processes, various disadvantages are encountered. For example, the dichlorobutenes employed as starting materials in the process of Sakomura et al. are expensive and the hydrolysis reaction results in formation of alkali metal chlorides which must be disposed of. Further, recovery of metal formate from the hydrolysis mixture requires neutralization with caustic. Accordingly, in the overall reaction scheme of the Sakomura et al. process, valuable chlorine and caustic are consumed and less valuable metal chlorides are formed. The process of Vasey et al. suffers from low yields and conversion rates as shown in the examples. Further, provision is not made for regeneration of starting materials. Such problems are avoided in the process of Childs; however, that process is relatively complex and the use of electricity for regeneration adds cost to the process.

Accordingly, it would be desirable to provide an improved process for preparation of alkenediols. It is an object of this invention to provide such a process. A further object of the invention is to provide an improved process for the preparation of high yields of alkenediols without consumption of costly reactants. A further object of the invention is to provide for the preparation of alkenediols according to a series of reactions wherein only conjugated diene, water and oxygen are consumed. A specific object of the invention is to provide an improved process for the preparation of 2-butene-1,4-diol wherein only 1,3-butadiene, water and oxygen are consumed. Other objects of the invention will be apparent to persons of skill in the art from the following description and the appended claims.

It has now been found that the objects of this invention can be attained by contacting dibromoalkenes with alkali metal formate under conditions effective to hydrolyze the dibromoalkenes to alkenediols. According to a preferred embodiment of the invention, dibromoalkenes prepared by bromination of conjugated diene with cupric bromide are hydrolyzed in the presence of aqueous alkali metal formate, and cuprous bromide, alkali metal bromide and formic acid generated in the bromination and hydrolysis steps are contacted with molecular oxygen under conditions effective to regenerate cupric bromide and sodium formate which can be re-used in bromination and hydrolysis.

Advantageously, preparation of alkenediols according to this invention results in high yields of the desired products. Further, according to a preferred embodiment of the invention, high yields of alkenediols are obtained according to an overall reaction scheme in which only conjugated diene, water and oxygen are consumed. The present invention gives particularly good results when employed in the production of 2-butene-1,4-diol from dibromobutenes as hydrolysis of the latter in the presence of alkali metal formate results in substantially complete hydrolysis of 1,4-dibromo-2-butene isomer to 2-butene-1,4-diol, and in addition, isomerization takes place such that at least a portion of any 3,4-dibromo-1-butene present in the intial charge is converted to 2-butene-1,4-diol. Accordingly, costly separation operations and the use of additional metals or compounds thereof are not required. According to a particularly advantageous embodiment of the invention, 2-butene-1,4-diol is prepared by a continuous process involving bromination of 1,3-butadiene in the presence of cupric bromide, followed by hydrolysis of the resulting dibromobutenes in the presence of alkali metal formate to form high yields of 2-butene-1,4-diol, with regeneration of cupric bromide and metal formate and recycle thereof. The process according to this aspect of the invention can be represented as follows:

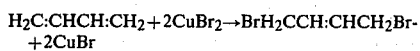

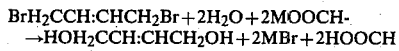

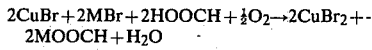

As used above, M represents alkali metal. The net reaction from the above is as follows:

$$H_2C{:}CHCH{:}CH_2 + H_2O + \tfrac{1}{2}O_2 \rightarrow HOH_2CCH{:}CHC{-}H_2OH$$

DESCRIPTION OF THE INVENTION

Broadly, the method of this invention comprises contacting dibromoalkene with alkali metal formate under hydrolysis conditions to form alkenediol. According to a more specific aspect of the invention, the dibromoalkene which is hydrolyzed in the presence of alkali metal formate is prepared by bromination of conjugated diene with cupric bromide, and the cuprous bromide formed as a by-product of the bromination step, as well as alkali metal bromide and formic acid by-products of the hydrolysis step are contacted with molecular oxygen under conditions effective to regenerate cupric bromide and alkali metal formate which can be re-used in bromination and hydrolysis.

In greater detail, alkali metal formates useful according to this invention include sodium formate, potassium formate, and other water-soluble alkali metal formates. Mixtures also can be used if desired. Sodium formate and potassium formate are preferred from the standpoint of cost and availability, best results being attained with sodium formate.

The dibromoalkene starting materials employed according to this invention are those containing 4 to about 12 carbon atoms corresponding to the formula $R_2BrCCR{:}CRCBrR_2$ or $R_2C{:}CRCBrRCBrR_2$ wherein each R is independently hydrogen or an alkyl radical of 1 to about 8 carbons. Mixtures of dibromoalkenes corresponding to the stated formulae and having identical R groups (e.g., a mixture of 1,4-dibromo-2-butene and 3,4-dibromo-1-butene) also can be used if desired. However, in order to maximize alkenediol yields, the dibromoalkene starting material preferably comprises a major portion of dibromoalkene of the formula $R_2BrCCR{:}CRCBrR_2$. More preferably, at least about 75 mole % of the initial dibromoalkene charge corresponds to such formula.

Specific examples of useful dibromoalkenes include 1,4-dibromo-2-butene, 3,4-dibromo-1-butene, 1,4-dibromo-2-pentene, 3,4-dibromo-1-pentene, 1,4-dibromo-2-hexene, 2,5-dibromo-3-hexene, 1,4-dibromo-2-methyl-2-hexene, 2,5-dibromo-3-octene, 4,7-dibromo-5-decene and 1,4-dibromo-2-dodecene. The present invention gives best results in production of 2-butene-1,4-diol from 1,4-dibromo-2-butene or mixtures thereof with up to about 20 mole % 3,4-dibromo-1-butene.

The dibromoalkenes employed as starting materials according to this invention can be prepared by any suitable means. Bromination of conjugated diene with suitable brominating agents such as molecular bromine or cupric bromide is preferred in order to obtain dibromoalkenes containing desirably high levels of the preferred dibromoalkene identified hereinabove. As discussed in greater detail hereinbelow, the dibromoalkenes employed according to this invention most preferably are prepared by bromination of conjugated diene in the presence of cupric bromide. Useful conjugated dienes are those containing 4 to about 12 carbon atoms such as 1,3-butadiene, 1,3-pentadiene, 1,3-hexadiene, 2,4-hexadiene, 2-methyl-1,3-hexadiene, 1,3-octadiene, 3,5-octadiene and 1,3-dodecadiene.

Reaction of dibromoalkenes with alkali metal formate according to this invention is conducted under conitions such that hydrolysis of the dibromoalkene takes place. Such conditions, also referred to herein as hydrolysis conditions, include relative proportions of alkali metal formate and dibromoalkene, concentration of formate salt in aqueous reaction medium, temperature, pressure and time, and are discussed in greater detail hereinbelow.

Preferably, at least about two moles alkali metal formate are used per mole dibromoalkene to ensure substantially complete conversion of dibromoalkene to alkenediol. Typically, conversion increases with increasing formate salt to dibromoalkene molar ratios, and accordingly, ratios in excess of about 2:1 are more preferred. Most preferably, the alkali metal formate to dibromoalkene molar ratio ranges from about 2.5:1 to about 10:1. Molar ratios of less than about 2:1 can be used if desired but are not preferred as conversion may be lower than desired.

Hydrolysis according to this invention is conducted under aqueous conditions. Water is used in an amount which is at least sufficient to maintain substantially all of the alkali metal formate employed in solution and avoid formation of undesirably high levels of formate esters during hydrolysis. Preferably, the amount of water is such that the concentration of alkali metal formate ranges from about 5 to about 30 wt. %. More preferably, this concentration ranges from about 6 to about 18 wt. %, with best results being attained from about 8 to about 15 wt. %. Water participates in the hydrolysis reaction, with two moles being required for conversion of each mole of dibromoalkene to alkenediol based upon reaction stoichiometry. The above-described alkali metal formate to dibromoalkene molar ratios and alkali metal formate concentrations are effective to ensure the presence of at least a stoichiometric amount of water.

Temperature in the hydrolysis reaction is sufficiently high to ensure reasonable reaction rates but not so high as to promote substantial decomposition of dibromoalkene starting material. Preferred temperatures range from about 80° to about 150° C. More preferably, the hydrolysis temperature is about 100° C.

Pressure in the hydrolysis reaction varies somewhat depending on temperature and, in general, is sufficiently high to maintain a liquid phase in the hydrolysis zone. Preferred hydrolysis pressure is about atmospheric.

Reaction time varies depending upon reactant proportions, temperature and rate of mixing of the reactants, and generally is sufficiently long to ensure substantial conversion of dibromoalkene to alkenediol. The hydrolysis reactants preferably are agitated in order to increase reaction rates.

Products of the hydrolysis reaction comprise a water and formic acid solution of alkenediol and alkali metal bromide. If alkali metal formate is used in excess of a stoichiometric amount, in the reaction mixture also contains soluble alkali metal formate. Separation of alkenediol from the hydrolysis product is preferably accomplished by distillation, although extraction, adsorption on active carbon and other suitable techniques also can be employed. Following separation of alkenediol, alkali metal formate, if present, can be recovered from the remaining hydrolysis product by filtration or other suitable solid-liquid separation techniques and re-used in hydrolysis.

According to a more specific aspect of the invention, alkenediols are produced according to a series of reactions, including the above-described hydrolysis reaction, in which only conjugated diene, oxygen, and water are consumed.

Briefly, the process according to this aspect of the invention comprises contacting conjugated diene with cupric bromide under bromination conditions to form dibromoalkene, contacting the resultant dibromoalkense with alkali metal formate under hydrolysis conditions to form alkenediols, and contacting cuprous bromide formed in the bromination step and alkali metal bromide and formic acid formed in the hydrolysis step with molecular oxygen under conditions effective to regenerate cupric bromide and alkali metal formate which can be recycled. If desired, regenerated cupric bromide and alkali metal formate can be separated prior to recycle. However, the presence of alkali metal formate during bromination does not hinder the bromination reaction, and accordingly, it is preferred to recycle both salts to the bromination step without separation.

In greater detail, the bromination step according to this aspect of the invention comprises contacting conjugated diene with cupric bromide under conditions effective to form dibromoalkenes. The reaction is conducted in the presence of an inert liquid medium in which the conjugated diene to be brominated is soluble. Suitable media include alkanes such as hexane, heptane and octane as well as various other materials which are substantially inert to the reactants employed and liquid at bromination temperatures, such as acetonitrile and dimethylformamide. Preferably, the medium is purified prior to use, for example by percolation through silica gel and/or molecular sieves, to remove traces of water and other impurities which may promote undesirable side reactions and otherwise interfere with the bromination reaction.

Conjugated dienes suitable for use according to this aspect of the invention are those containing 4 to about 12 carbon atoms, specific examples of which are identified hereinabove. Gaseous dienes are charged under pressure sufficient to solubilize the same in the reaction medium, but not so high as to promote substantial oligomerization of the diene, although it is contemplated to employ inhibitors capable of retarding oligomerization without interfering with the bromination reaction to facilitate the use of higher diene pressures. Preferably, gaseous conjugated dienes are charged to the bromination zone under pressure of about 1 to about 6 atmospheres (about 1 to about 6.2 kg/cm$^2$) to ensure solubilization without the need for oligomerization inhibitors. Liquid conjugated dienes can be charged under pressure if desired though this is neither necessary nor preferred.

From the reaction stoichiometry, two moles of cupric bromide are required for bromination of each mole of conjugated diene. However, in order to avoid promotion of side reactions and formation of brominated alkanes, it is desirable to employ the conjugated diene in excess of the stoichiometric amount. Preferably, the molar ratio of conjugated diene to cupric bromide is at least about 0.52:1. More preferably, this ratio ranges from about 0.52:1 to about 5:1, although a substantially greater proportion of diene can be used if desired and often gives particularly good results in continuous processes.

Bromination temperatures are sufficiently high to ensure reasonable reaction rates but not so high as to promote substantial oligomerization of conjugated diene. Again, it is contemplated to employ suitable inhibitors to retard oligomerization and thereby facilitate the use of higher temperatures. Preferred bromination temperatures range from about 75 to about 150° C., with best results being attained at about 100° C.

In batch processes, the time of the bromination reaction varies depending on temperatures, reactant proportions, etc. and generally is sufficient to allow for substantially complete conversion of diene to alkenediol. Residence time in the bromination zone can be regulated as desired in continuous processes.

Although not required, all or a portion of the alkali metal formate to be used in the hydrolysis step can be present during the bromination step if desired. The presence of alkali metal formate during bromination does not hinder the bromination reaction, and while some formate esters may form, this typically is of no consequence because the same are subsequently hydrolyzed. Conveniently, a combination of cupric bromide and alkali metal formate is added to the bromination zone, although it also is contemplated to add cupric bromide separate from the alkali metal formate. In a particularly preferred operational mode discussed in greater detail hereinbelow, continuous production of alkenediol is accomplished by adding an initial charge of cupric bromide and alkali metal formate to a bromination zone, subsequently regenerating cupric bromide and alkali metal formate from bromination and hydrolysis by-products, and then recycling regenerated cupric bromide and alkali metal formate to the bromination zone.

The product of the bromination step comprises solid cuprous bromide and a solution of soluble dibromoalkenes in the reaction medium. Alkali metal formate, if present in the bromination step also is included in the reaction mixture in the form of a solid. Reaction medium is removed from the bromination product, preferably by distillation, and the medium can be condensed and recycled to the bromination zone if desired.

The remaining bromination product, comprising dibromoalkene, solid cuprous bromide and, if present during the bromination step, solid alkali metal formate, then is passed to a hydrolysis zone which is provided with sufficient water and alkali metal formate for the hydrolysis step. Of course, if the bromination product already contains sufficient alkali metal formate for hydrolysis, there is no need for further addition of formate salt. Relative proportions of dibromoalkene and alkali metal formate and aqueous alkali metal formate concentrations in the hydrolysis step are as discussed hereinabove.

Hydrolysis is conducted by reacting dibromoalkene, alkali metal formate and water under hydrolysis conditions, as described hereinabove, to form a reaction mixture comprising a water and formic acid solution of alkenediol, excess alkali metal formate and alkali metal bromide as well as insoluble cuprous bromide. Water, formic acid and a major portion of alkenediol are separated from the hydrolysis product, preferably, by vacuum distillation so that separation can be accomplished at temperatures low enough to avoid promotion of undesirable side reactions, e.g., below about 150° C. Subsequently, the recovered water, formic acid and alkenediol are further separated into an alkenediol stream and a water and formic acid stream, preferably by fractional distillation. Preferably, a major portion of the water and formic acid recovered from the hydrolysis step is used in regeneration as described in greater detail hereinbelow.

The hydrolysis product remaining after separation of alkenediol, water and formic acid comprises a concentrated slurry of cuprous bromide, alkali metal bromide and excess alkali metal formate in alkenediol. Solids are separated from the slurry, preferably by filtration, and residual alkenediol is removed from the resulting solids, preferably by washing the same with a portion of the water and formic acid stream recovered from the hydrolysis product. Of course, fresh water and formic acid or other suitable wash media, such as lower aliphatic alcohols, can be used if desired; however, process efficiency is optimized through the use of a portion of the recovered water and formic acid stream as the wash liquid. After separation of the wash filtrate, the remaining solids are conveyed to a regeneration zone and contacted therein with molecular oxygen in the presence of formic acid under regeneration conditions. Preferably, water also is present during regeneration. Conveniently, formic acid and water used in regeneration are supplied by the water and formic acid stream recovered from the hydrolysis product.

Molecular oxygen is charged to the regeneration zone in an amount sufficient to ensure reasonable reaction rates but not so high as to create a flammable mixture of oxygen and formic acid or cause oxidation of formic acid to carbon dioxide and water. Preferably, oxygen partial pressures range from about 20 to about 40 psig. Most conveniently, molecular oxygen is supplied to the regeneration zone in the form of air, although other sources are contemplated. In addition, one or more diluent gases can be charged to the regeneration zone to increase overall pressure while maintaining nonflammable levels of oxygen. Suitable diluent gases include ethane and other hydrocarbons which are inert to the regeneration reactants and remain in the gaseous state under regeneration conditions.

The amounts of formic acid and, if used, water employed in regeneration are at least sufficient to provide for substantial conversion of alkali metal bromide and cuprous bromide to alkali metal formate and cupric bromide without substantial oxidation of formic acid. Preferably, from about 0.5 to about 5 moles formic acid are used per mole of alkali metal bromide and up to about 1 mole of water is present per mole of formic acid. More preferably, the molar ratio of formic acid to alkali metal bromide ranges from about 1:1 to about 2:1 and the molar ratio of water to formic acid ranges from about 0.005:1 to about 0.5:1. In continuous processes wherein formic acid and water for regeneration are supplied by a formic acid and water stream separated from the hydrolysis product, the latter can be adjusted to provide the desired amounts of water and/or formic acid to the regeneration zone with addition of water or formic acid as necessary to provide the desired water to formic acid ratio.

Regeneration temperatures are sufficiently high to ensure reasonable reaction rates without promoting substantial oxidation of formic acid. Preferred temperatures range from about 80° to about 120° C., best results being achieved at about 100° C.

As a result of the regeneration step, cuprous bromide formed during the bromination step is oxidized to cupric bromide and alkali metal bromide formed during hydrolysis is converted to alkali metal formate. These salts are separated from excess formic acid and water present in regeneration, for example by distillation, and then dried. Water and formic acid preferably are condensed and recycled to the hydrolysis zone. Dried cupric bromide and alkali metal formate preferably are recycled to the bromination zone either in solid form or as a slurry in a liquid suitable for use as reaction medium in the bromination step.

The present invention gives best results in the continuous production of 2-butene-1,4-diol such that only 1,3-butadiene, oxygen and water are consumed. This embodiment of the invention is described in greater detail in conjunction with the drawing.

To agitated bromination zone 1 containing hexane, cupric bromide and sodium formate, and maintained at bromination temperature, is charged 1,3-butadiene through line 3 under pressure sufficient to solubilize the diene in the hexane without oligomerization of diene.

Bromination product, comprising solid cuprous bromide and sodium formate as well as a hexane solution of mixed dibromobutene isomers rich in 1,4-dibromo-2-butene is passed from the bromination zone through line 5 to tower 7. In the tower, hexane is stripped from the bromination product and returned to bromination zone 1 via line 9.

Tower bottoms, comprising cuprous bromide, sodium formate and dibromobutenes are passed through line 11 to agitated hydrolysis reactor 17. Water is added through line 13 and recycle water and formic acid are supplied through line 15.

The reaction mixture is subjected to hydrolysis conditions in hydrolysis reactor 17 with the result that 1,4-dibromo-2-butene is substantially converted to 2-butene-1,4-diol and 3,4-dibromo-1-butene is converted primarily to 1-butene-3,4-diol but with some isomerization to 2-butene-1,4-diol.

The hydrolysis product, comprising mixed butenediol isomers rich in 2-butene-1,4-diol, sodium formate and sodium bromide dissolved in formic acid and water, plus solid cuprous bromide is passed through line 19 to tower 21 in which water, formic acid and most of the butenediol are vacuum distilled. Distillate is passed through line 23 to tower 25 in which water and formic acid are distilled. Liquid butenediol is removed from tower 25 via line 27 to purification and/or storage equipment (not shown).

Bottoms from tower 21, comprising a concentrated butenediol slurry of cuprous bromide, sodium bromide and sodium formate pass to filter 31 via line 29. A portion of the water and formic acid recovered in tower 25 is added to the filter via lines 33 and 35.

In filter 31, bottoms from tower 21 are washed with formic acid and water to remove residual butenediol. Wash filtrate, comprising water, formic acid and a minor amount of butenediol, is returned to tower 21 via lines 39 and 19.

Solids from filter 31 are passed via line 37 to line 33 which carries a major portion of the water and formic acid recovered in tower 25. A water and formic acid slurry of cuprous bromide, sodium bromide and sodium formate pass to agitated regeneration zone 41 via line 33.

Air is charged to the regeneration zone through line 43 and the contents are subjected to regeneration conditions to oxidize cuprous bromide to cupric bromide and convert sodium bromide to sodium formate.

The regeneration product is passed through line 45 to tower 47 in which water and formic acid are stripped. These are recycled to the hydrolysis reactor via line 15. Tower bottoms, comprising cupric bromide and sodium formate are conveyed to dryer 49, dried, and then recycled to bromination reactor 1.

The following examples illustrate the present invention, it being understood that the same are not to be construed as limiting the scope of the invention.

EXAMPLE I

To a 300 ml glass pressure bottle equipped with mechanical stirrer, thermocouple, gas inlet and pressure gauge were added 34.9 g n-heptane followed by 22.3 g (0.10 mole) cupric bromide. The bottle then was placed in dry ice and 0.057 mole (3.078 g) 1,3-butadiene were metered into the bottle using a wet test meter. The pressure bottle was removed from the dry ice and heated to 100° C. with stirring. Heating at 100° C. and stirring were continued for 1¾ hours.

During heating a maximum pressure of 21 psig was attained. By the end of the run, pressure had decreased to 8 psig. Based on the rate of pressure drop, at least 77 mole % of the 1,3-butadiene was consumed during the first 30 minutes of heating.

Following heating the reaction product was analyzed by gas chromatography using a 10% DEGS-PS, 6 foot glass column. Analysis showed that 0.0492 mole dibromobutenes were produced. This corresponds to a 98 mole % yield based upon the limiting reagent, cupric bromide. Distribution of dibromobutene isomers was determined by gas chromatography, again using a 10% DEGS-PS, 6 foot glass column. Results were as follows: 67% trans-1,4-dibromo-2-butene, 12% cis-1,4-dibromo-2-butene, and 21% 3,4-dibromo-1-butene.

EXAMPLE II

The procedure of EXAMPLE I was repeated except that the initial amount of 1,3-butadiene was decreased to 0.0404 mole such that the diene was the limiting reagent. 0.0379 mole dibromobutenes were produced corresponding to a 94 mole % yield based on the initial charge of 1,3-butadiene. Isomer distribution was as in EXAMPLE I.

EXAMPLE III

Bromination was conducted substantially as described in EXAMPLE I. The product was filtered to remove cuprous bromide and then stripped of heptane solvent. Analysis of the product as in EXAMPLE I showed 79% 1,4-dibromo-2-butene and 21% 3,4-dibromo-2-butene.

15.5 g (0.0725 mole) of the dibromobutenes produced in the bromination step were added to a solution of 10 g (0.147 mole) sodium formate in 50 ml water in a large glass flask. The hydrolysis mixture then was heated at the reflux temperature for 2½ hours. After heating there resulted a clear, slightly yellow solution containing a few small droplets of a second phase. Analysis of the solution by gas chromatography according to the procedure of EXAMPLE I showed no dibromobutenes and an 88 mole % yield of butenediol isomers based upon the initial dibromobutene charge. The distribution of butenediol isomers was 92% 2-butene-1,4-diol and 8% 1-butene-3,4-diol.

EXAMPLE IV

The procedure of EXAMPLE III was repeated except that in the hydrolysis step only trans-1,4-dibromo-2-butene was used and the sodium formate to trans-1,4-dibromo-2-butene molar ratio was 4.4:1. Analysis of product showed a 94 mole % yield of butenediol isomers based upon the initial dibromobutene charge. Isomer distribution was 93% 2-butene-1,4-diol and 7% 1-butene-3,4-diol.

EXAMPLE V

Regeneration of cuprous bromide and sodium formate from by-products of the bromination and hydrolysis steps was demonstrated as follows. To a jacketed, 1 liter, titanium, stirred autoclave equipped with reflux condensor and gas inlets were added 42.9 g (0.30 mole) cuprous bromide, 30.9 g (0.30 mole) sodium bromide, 13.8 g (0.30 mole) formic acid, 81.6 g (1.2 moles) sodium formate and 300 g water at ambient temperature (22°–25° C.). Temperature then was increased to 100° C. and a gaseous mixture of 80 vol. % ethane, 15 vol. % butadiene and 5 vol. % $O_2$ was charged to the autoclave at a rate of 120 STP 1/hr. After 30 minutes the contents of the autoclave were analyzed for copper (II) ions by iodometry. Analysis showed Cu(II) corresponding to a 90 mole % yield of cupric bromide based upon the starting amount of cuprous bromide.

I claim:

1. A process for production of alkenediol comprising (A) contacting conjugated diene of 4 to about 12 carbon atoms with cupric bromide under bromination conditions; (B) contacting a product from (A) comprising dibromoalkene containing 4 to about 12 carbon atoms corresponding to the formula $R_2BrCCR:CRCBrR_2$ or $R_2C:CRCBrRCBrR_2$ wherein each R is independently hydrogen or an alkyl radical of 1 to about 8 carbon atoms consistent with the conjugated diene employed in (A), or a mixture of dibromoalkenes of said formulae wherein the R groups are identical, with alkali metal formate under hydrolysis conditions; (C) separating alkenediol from the product of (B); and (D) contacting cuprous bromide, alkali metal bromide and formic acid by-products from steps (A) and (B) with molecular oxygen under conditions effective to regenerate cupric bromide and alkali metal formate.

2. The process of claim 1 wherein the alkali metal formate is sodium formate.

3. The process of claim 1 wherein the conjugated diene is 1,3-butadiene.

4. The process of claim 3 wherein the alkali metal formate is sodium formate.

5. The process of claim 1 wherein a major portion of the dibromoalkene employed in (B) corresponds to the formula $R_2BrCCR:CRCBrR_2$.

6. The process of claim 1 wherein at least 75 mole % of the dibromoalkene employed in (B) corresponds to the formula $R_2BrCCR:CRCBrR_2$.

7. The process of either of claims 5 or 6 wherein said dibromoalkene corresponding to the formula $R_2BrCCR:CRCBrR_2$ is 1,4-dibromo-2-butene.

8. The process of claim 1 wherein the dibromoalkene employed in (B) is 1,4-dibromo-2-butene.

9. A process for production of alkenediol comprising:
(A) contacting conjugated diene of 4 to about 12 carbon atoms with cupric bromide under bromination conditions in an inert liquid medium;
(B) contacting the product from (A) with alkali metal formate under hydrolysis conditions;
(C) separating alkenediol from the product of (B); and
(D) contacting solid cuprous bromide, alkali metal bromide and formic acid remaining after separation in (C) with molecular oxygen under conditions effective to regenerate cupric bromide and alkali metal formate.

10. The process of claim 9 wherein the conditions in (A) comprise a conjugated diene to cupric bromide molar ratio of about 0.52:1 to about 5:1 and a temperature of about 75° to about 150° C.

11. The process of claim 9 wherein the conditions in (B) comprise an alkali metal formate to dibromoalkene molar ratio of at least about 2:1, a concentration of alkali metal formate in water of about 5 to about 30 wt. %, and a temperature of about 80° to about 150° C.

12. The process of claim 9 wherein the conditions in (D) comprise a molecular oxygen partial pressure of about 20 to about 40 psig., a formic acid to alkali metal bromide molar ratio of about 0.5:1 to about 5:1 and a temperature of about 80° to about 120° C.

13. The process of claim 9 wherein alkali metal formate is present in (A).

14. The process of claim 9 wherein cupric bromide and alkali metal formate from (D) are recycled to (A).

15. The process of claim 9 wherein the conjugated diene is 1,3-butadiene.

16. A process for production of 2-butene-1,4-diol comprising the steps:
(A) contacting 1,3-butadiene and cupric bromide in the presence of alkali metal formate and an inert liquid solvent for 1,3-butadiene under bromination conditions to form a reaction mixture comprising dibromobutenes, cuprous bromide and alkali metal formate;
(B) substantially separating inert hydrocarbon solvent from the reaction mixture of (A);
(C) combining the product remaining after separation in (B) with a solution of formic acid in water under hydrolysis conditions to form a reaction mixture comprising water, formic acid, 2-butene-1,4-diol, alkali metal formate, alkali metal bromide and cuprous bromide;
(D) separating formic acid, water and a major portion of 2-butene-1,4-diol from the reaction mixture of (C) to form a concentrated slurry comprising alkali metal formate, alkali metal bromide, cuprous bromide and 2-butene-1,4-diol;
(E) separating 2-butene-1,4-diol from the formic acid and water of (D);
(F) contacting alkali metal formate, alkali metal bromide and cuprous bromide from (D) with molecular oxygen in the presence of formic acid and water under conditions effective to regenerate cupric bromide and alkali metal formate;
(G) recycling cupric bromide and alkali metal formate from (F) to (A).

17. The process of claim 16 wherein the concentrated slurry in (D) is washed with water and formic acid from (E) prior to contacting with molecular oxygen in (F).

18. The process of claim 17 wherein the formic acid and water in (F) are supplied by the water and formic acid recovered in (E).

19. The process of claim 16 wherein the formic acid and water in (F) are supplied by the water and formic acid recovered in (E).

20. The process of claim 16 wherein cupric bromide and alkali metal formate from (F) are recycled to (A) in an inert liquid medium which is the same as the inert liquid medium in (A).

21. The process of claim 16 wherein the alkali metal formate is sodium formate.

* * * * *

UNITED STATES PATENT OFFICE
CERTIFICATE OF CORRECTION

Patent No. 4,306,100                      Dated    December 15, 1981

Inventor(s)     GEORGE R. WOOD

It is certified that error appears in the above-identified patent and that said Letters Patent are hereby corrected as shown below:

Patent

Page 1, Abstract, lines 1 and 2 "of a dibromoalkenes" should be --of dibromoalkenes--

| Column | Line | |
|---|---|---|
| 2 | 62 | "$CHCH_2Br-$" should be --$CHCH_2Br$-- |
| 2 | 64 | "MOOCH-" should be --MOOCH-- |
| 2 | 66 | "$2CuBr_2+-$" should be --$2CuBr_2+$-- |
| 3 | 68 | "coni-" should be --condi-- |
| 4 | 57 | "amount, in the" should read --amount, the-- |
| 5 | 7-8 | "dibromoalk-ense" should be --dibromoalkenes-- |

Signed and Sealed this

Ninth Day of November 1982

[SEAL]

Attest:

GERALD J. MOSSINGHOFF

Attesting Officer     Commissioner of Patents and Trademarks